US012651475B2

(12) United States Patent
Sabapathy et al.

(10) Patent No.: US 12,651,475 B2
(45) Date of Patent: Jun. 9, 2026

(54) METHOD FOR EXTRACTING PROBLEM LIST SECTION FROM UNSTRUCTURED DATA IN MEDICAL RECORD DOCUMENT, AND OUTPUTTING PORTION OF PROBLEM LIST SECTION BY PROCESSORS

(71) Applicant: Optum, Inc., Minnetonka, MN (US)

(72) Inventors: Rajesh Sabapathy, Gurgaon (IN); Chirag Mittal, Gurgaon (IN); Gourav Awasthi, Gurugram (IN); Chandni Nanda, Delhi (IN); Ravi Pande, Gautam Budh Nagar (IN); Vaibhav Kakkar, Irvine, CA (US); Mohit Singhal, Delhi (IN); Rahul Bhaskar, Irvine, CA (US)

(73) Assignee: Optum, Inc., Minnetonka, MN (US)

( * ) Notice: Subject to any disclaimer, the term of this patent is extended or adjusted under 35 U.S.C. 154(b) by 298 days.

(21) Appl. No.: 18/472,911

(22) Filed: Sep. 22, 2023

(65) Prior Publication Data

US 2024/0331434 A1     Oct. 3, 2024

Related U.S. Application Data

(60) Provisional application No. 63/493,529, filed on Mar. 31, 2023.

(51) Int. Cl.
| | |
|---|---|
| *G06V 30/416* | (2022.01) |
| *G06V 30/10* | (2022.01) |
| *G16H 10/60* | (2018.01) |
| *G16H 70/60* | (2018.01) |
| *G06V 30/146* | (2022.01) |
| *G06V 30/148* | (2022.01) |

(52) U.S. Cl.
CPC ............ *G06V 30/416* (2022.01); *G06V 30/10* (2022.01); *G16H 10/60* (2018.01); *G16H 70/60* (2018.01); *G06V 30/1478* (2022.01); *G06V 30/153* (2022.01)

(58) Field of Classification Search
None
See application file for complete search history.

(56) References Cited

U.S. PATENT DOCUMENTS

| | | | |
|---|---|---|---|
| 10,997,223 B1 * | 5/2021 | Christodoulopoulos | ................... G06F 40/295 |
| 11,481,411 B2 | 10/2022 | Sethumadhavan et al. | |
| 2009/0063189 A1 | 3/2009 | Hupke et al. | |

(Continued)

*Primary Examiner* — Haris Sabah
(74) *Attorney, Agent, or Firm* — Bookoff McAndrews, PLLC

(57) ABSTRACT

A computer-implemented method for identifying a problem list section from an electronic document includes receiving, by one or more processors, the electronic document, generating, by the one or more processors and based on applying an optical character recognition algorithm to the electronic document, unstructured text, and identifying, by the one or more processors, one or more problem list words in the unstructured text, the one or more problem list words belonging in a dataset for identifying a presence of a problem list section. The method also includes associating, by the one or more processors, a portion of the unstructured text that corresponds to the one or more problem list words in the unstructured text with the problem list section and outputting, by the one or more processors, at least a portion of the problem list section.

20 Claims, 6 Drawing Sheets

(56)  References Cited

U.S. PATENT DOCUMENTS

| | | |
|---|---|---|
| 2019/0006027 A1 | 1/2019 | Sacaleanu et al. |
| 2020/0312463 A1* | 10/2020 | Bronkalla ............... G06F 40/20 |
| 2022/0058383 A1* | 2/2022 | Seth ................. G06V 30/19107 |
| 2023/0368553 A1* | 11/2023 | Jha .......................... G06F 17/14 |

* cited by examiner

Figure 3:
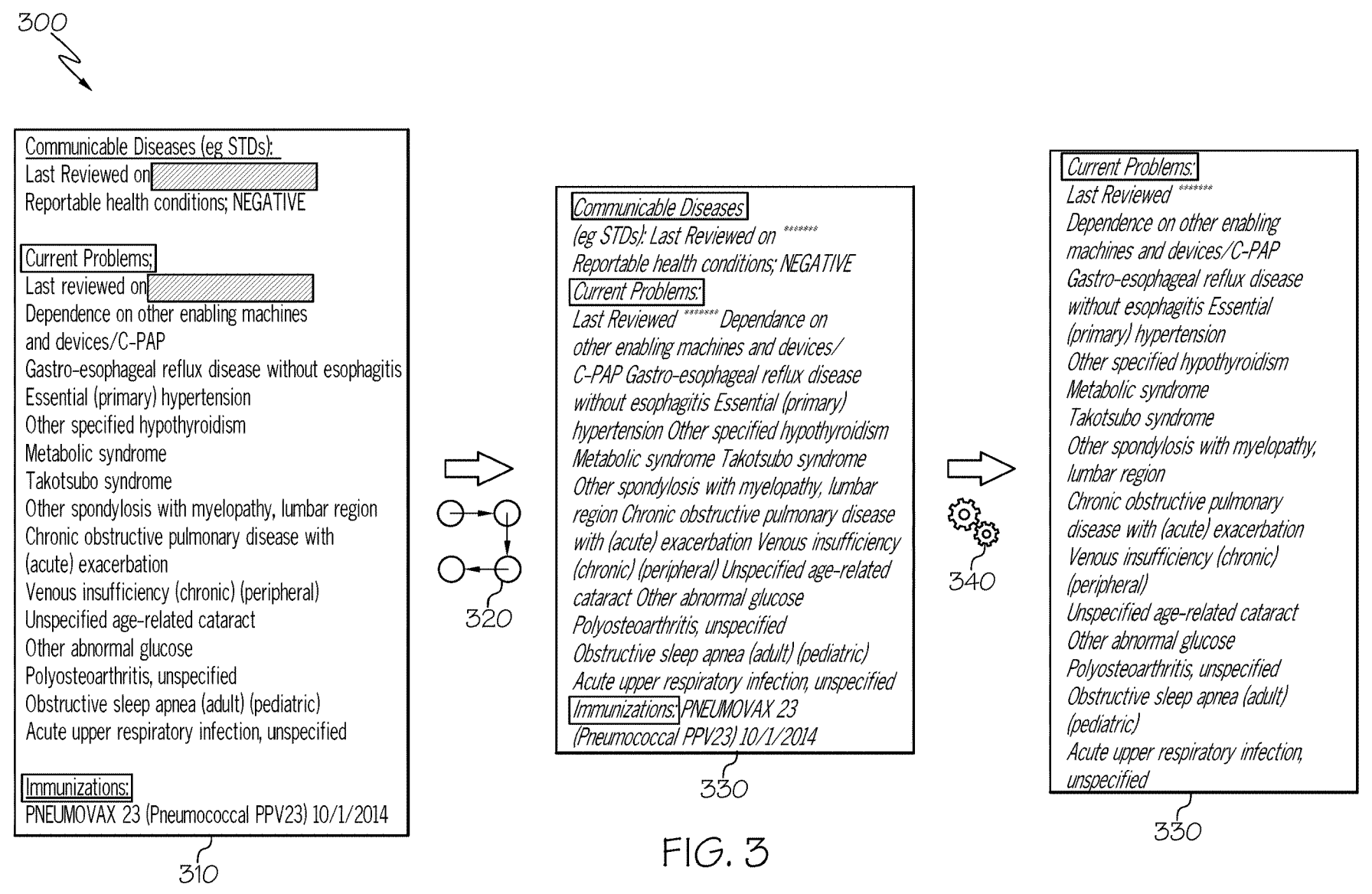

300

310

Communicable Diseases (eg STDs):
Last Reviewed on [____]
Reportable health conditions; NEGATIVE Current Problems:
Last reviewed on [____]
Dependence on other enabling machines
and devices/C-PAP
Gastro-esophageal reflux disease without esophagitis
Essential (primary) hypertension
Other specified hypothyroidism
Metabolic syndrome
Takotsubo syndrome
Other spondylosis with myelopathy, lumbar region
Chronic obstructive pulmonary disease with
(acute) exacerbation
Venous insufficiency (chronic) (peripheral)
Unspecified age-related cataract
Other abnormal glucose
Polyosteoarthritis, unspecified
Obstructive sleep apnea (adult) (pediatric)
Acute upper respiratory infection, unspecified Immunizations:
PNEUMOVAX 23 (Pneumococcal PPV23) 10/1/2014

320

330

Communicable Diseases
(eg STDs): Last Reviewed on
Reportable health conditions; NEGATIVE Current Problems:
Last Reviewed ******* Dependance on
other enabling machines and devices/
C-PAP Gastro-esophageal reflux disease
without esophagitis Essential (primary)
hypertension Other specified hypothyroidism
Metabolic syndrome Takotsubo syndrome
Other spondylosis with myelopathy, lumbar
region Chronic obstructive pulmonary disease
with (acute) exacerbation Venous insufficiency
(chronic) (peripheral) Unspecified age-related
cataract Other abnormal glucose
Polyosteoarthritis; unspecified
Obstructive sleep apnea (adult) (pediatric)
Acute upper respiratory infection, unspecified
Immunizations: PNEUMOVAX 23
(Pneumococcal PPV23) 10/1/2014

340

330

Current Problems:
Last Reviewed *******
Dependence on other enabling
machines and devices/C-PAP
Gastro-esophageal reflux disease
without esophagitis Essential
(primary) hypertension
Other specified hypothyroidism
Metabolic syndrome
Takotsubo syndrome
Other spondylosis with myelopathy,
lumbar region
Chronic obstructive pulmonary
disease with (acute) exacerbation
Venous insufficiency (chronic)
(peripheral)
Unspecified age-related cataract
Other abnormal glucose
Polyosteoarthritis, unspecified
Obstructive sleep apnea (adult)
(pediatric)
Acute upper respiratory infection,
unspecified

RECEIVE MEDICAL RECORDS — _410_

RECOGNIZE CHARACTERS — _420_

GENERATE LIST OF POTENTIAL PROBLEM LIST HEADINGS — _430_

EVALUATE LIST OF POTENTIAL PROBLEM LIST HEADINGS — _440_

GENERATE AND/OR REVISE LIST OF PROBLEM LIST HEADINGS — _450_

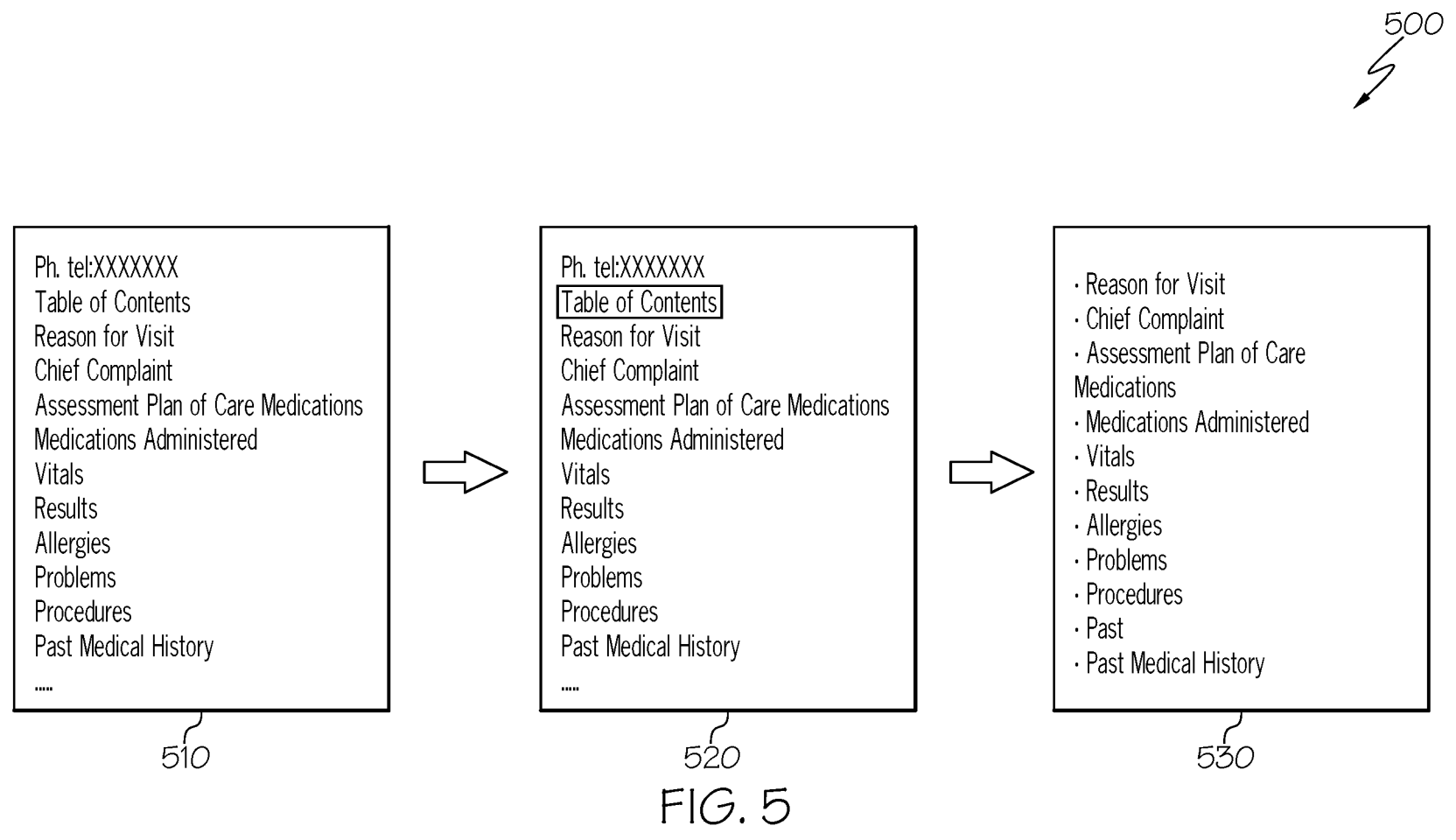

500

510

Ph. tel:XXXXXX
Table of Contents
Reason for Visit
Chief Complaint
Assessment Plan of Care Medications
Medications Administered
Vitals
Results
Allergies
Problems
Procedures
Past Medical History
.....

520

Ph. tel:XXXXXX
Table of Contents
Reason for Visit
Chief Complaint
Assessment Plan of Care Medications
Medications Administered
Vitals
Results
Allergies
Problems
Procedures
Past Medical History
.....

530

· Reason for Visit
· Chief Complaint
· Assessment Plan of Care Medications
· Medications Administered
· Vitals
· Results
· Allergies
· Problems
· Procedures
· Past
· Past Medical History

FIG. 5

METHOD FOR EXTRACTING PROBLEM LIST SECTION FROM UNSTRUCTURED DATA IN MEDICAL RECORD DOCUMENT, AND OUTPUTTING PORTION OF PROBLEM LIST SECTION BY PROCESSORS

CROSS-REFERENCE TO RELATED APPLICATION(S)

This application claims the benefit of priority to U.S. provisional patent application No. 63/493,529, filed on Mar. 31, 2023, the entirety of which is incorporated by reference.

TECHNICAL FIELD

The present disclosure relates generally to data analysis. More particularly, the present disclosure relates to systems and methods for extracting sections from unstructured data, and more specifically, for extracting sections from unstructured data pertaining to medical records.

BACKGROUND

Service providers, including medical service providers, receive numerous documents which require processing. Often, these documents are in the form of medical records ("MRs"). Some entities process large numbers of medical records. For example, an average of 10 million medical charts may be processed on an annual basis to identify Hierarchical Condition Categories ("HCCs") and/or International Classification of Diseases and Related Health Problems ("ICD"), which are used to determine risk-adjusted reimbursements from Centers for Medicare and Medicaid Services ("CMS").

Typically, a document like an MR for an individual contains several types of information, including the individual's present and past medical history. The MR can include a "Problem List" section that contains information about present health condition(s) of the individual. These health conditions are, at times, referred to herein as "problems." While MRs can contain one or more problems, MRs often contain additional types of information that is not relevant to the service provider processing the MR. For example, the service provider may be interested in evaluating diagnosis codes that can be extracted from these problem list sections to identify respective HCC codes (and/or ICD codes), which will be further reviewed by the coders. Potential "Problem List" sections to be extracted can be of following forms: "Active Problems," "Current Problems," "Problem," etc. Some processes involve use of an AI process or other automation to assist the coders, for example generating a set of pages and one or more potential HCC codes.

While automated processes for identifying sets of pages are helpful, they can be inaccurate when predicting HCCs and when identifying pages containing potential problems. For example, problem list identification and extraction from MRs is challenging (e.g., inaccurate, time consuming, and/or compute-resource intensive) due to various reasons, including:

The length of the document can range from 1 to 80 pages (or more).

The format of the document after extracting text can be unstructured and contain free flow text.

MRs have different templates that are followed by the producer of the MR (e.g., a medical provider or lab) while creating medical records.

Problem list heading terminology can have many variants. For example: "active problems," "problem list," "current problems," etc.

Lengths of problem list sections are not standardized and differ from document to document.

In some cases, hard copies of the MR are scanned and the OCR text lacks the structure contained in the original machine-readable document.

In addition to the above-described technical problems, existing solutions can themselves introduce technical drawbacks, such as being programmed for over-inclusive processing (e.g., analyzing all sections present within a document which may include irrelevant data) and inaccurate or inefficient processing (e.g., tagging incorrect or irrelevant HCC codes, sub-optimal parallel processing techniques applied to multiple documents), which can lead to long processing time and/or manual review of the documents (e.g., from coders).

This disclosure is directed to addressing the above-referenced and non-limiting technical challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

The present disclosure addresses the technical problem(s) described above or elsewhere in the present disclosure and improves the state of conventional character recognition techniques, such as those used in the healthcare industry. In some embodiments, the present disclosure teaches systems and methods for section identification in unstructured data.

In one aspect, a computer-implemented method for identifying a problem list section from an electronic document may include receiving, by one or more processors, the electronic document, generating, by the one or more processors and based on applying an optical character recognition algorithm to the electronic document, unstructured text, and identifying, by the one or more processors, one or more problem list words in the unstructured text, the one or more problem list words belonging in a dataset for identifying a presence of a problem list section. The method may also include associating, by the one or more processors, a portion of the unstructured text that corresponds to the one or more problem list words in the unstructured text with the problem list section and outputting, by the one or more processors, at least a portion of the problem list section.

In another aspect, a system for identifying a problem list section may include a memory storing instructions and a processor executing the instructions to perform a process including: receiving an electronic document, generating, based on applying an optical character recognition algorithm to the electronic document, unstructured text, and identifying one or more problem list words in the unstructured text, the one or more problem list words belonging in a dataset for identifying a presence of a problem list section. The process may further include associating a portion of the unstructured text that corresponds to the one or more problem list words in the unstructured text with the problem list section and outputting at least a portion of the problem list section.

In yet another aspect, a computer-implemented method for generating a list of problem list headings may include receiving, by one or more processors, an electronic document, recognizing, by the one or more processors, characters present in the electronic document by implementing an optical character recognition algorithm that receives the electronic document as an input and produces unstructured text as an output, and identifying, by the one or more processors, characters forming words and/or phrases of one or more headings that each indicate the presence of a problem list in the unstructured text output from the electronic document, each of the one or more headings being a potential problem list heading. The method may further include generating, by the one or more processors, a list of words and/or phrases that include the one or more potential problem list headings, the list of words and/or phrases forming a list of problem list headings, wherein one or more additional electronic documents are processed based on the list of problem list headings.

It is to be understood that both the foregoing general description and the following detailed description are example and explanatory only and are not restrictive of the detailed embodiments, as claimed.

BRIEF DESCRIPTION OF THE DRAWINGS

The accompanying drawings, which are incorporated in and constitute a part of this specification, illustrate various example embodiments and together with the description, serve to explain the principles of the disclosed embodiments.

FIG. 3 is a diagram of an example process for identifying a problem list in a medical record, according to some embodiments of the disclosure.

FIG. 5 is a diagram of an example process for generating and/or revising a list of headings, according to some embodiments of the disclosure.

DETAILED DESCRIPTION

Figure 1:
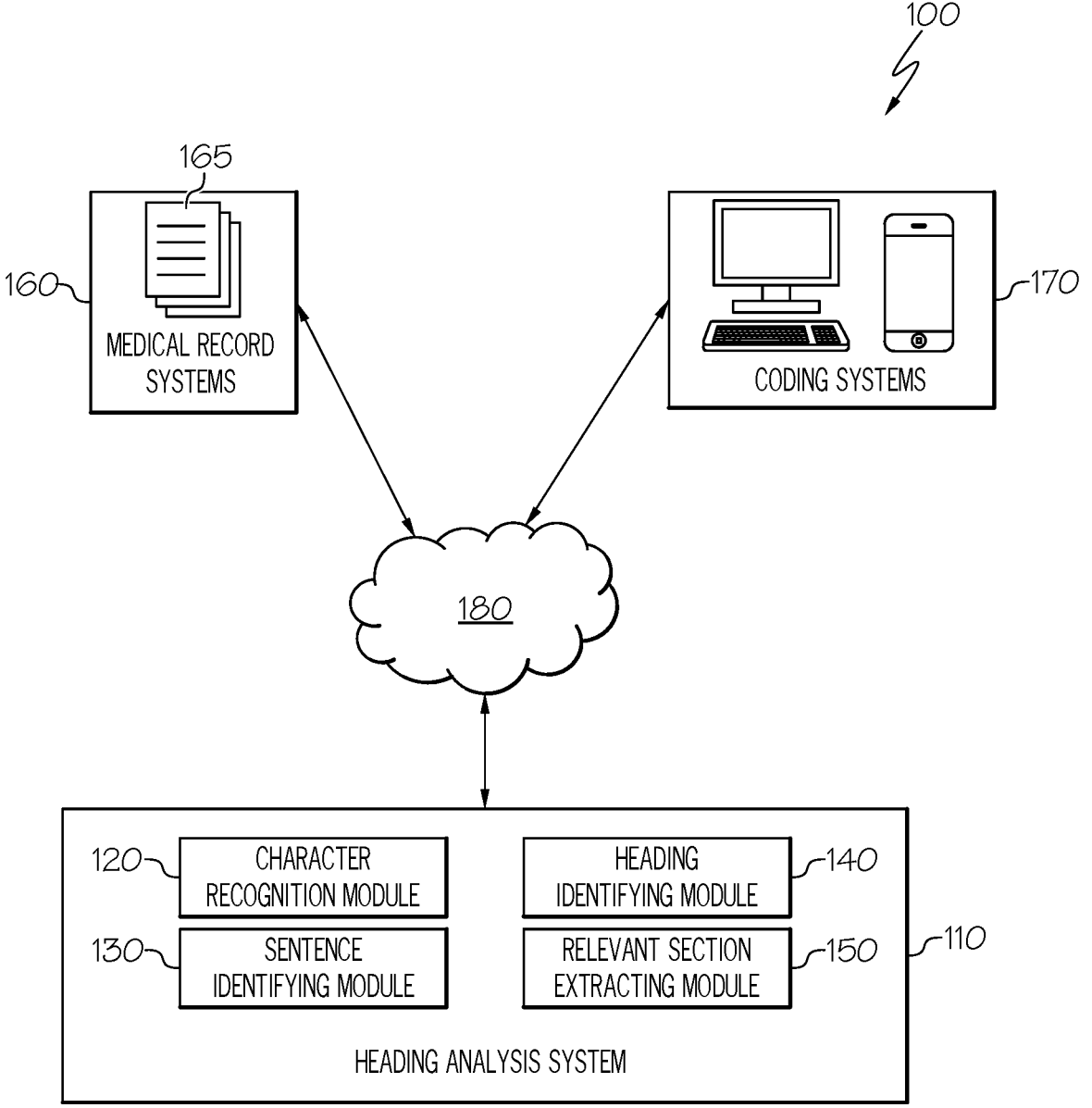
FIG. 1 is a diagram showing an example of a system that is capable of section identification in unstructured data, according to some embodiments of the disclosure.

Various embodiments of this disclosure relate generally to techniques for section identification, and, more particularly in some embodiments, to systems and methods for identifying sections in unstructured data.

As discussed above, conventional automations are unable to accurately identify sections in documents (e.g., MRs). In particular, conventional automated systems are unable to accurately identify problem lists in medical records ("MRs"). One challenge is due to the different terminology, different organization and formatting, and different length of various MRs.

Techniques disclosed herein may address these technical issues, providing technical improvements over conventional methodology. For example, use of character recognition may readily identify content within a document. This may be performed with a light-weight character recognition algorithm that is able to rapidly analyze certain portions of an electronic document without the need to output markup, data associated with the document's layout, or other information related to structure. Thus, the content within the document that is automatically detected is unstructured, and can be analyzed for headings associated with a problem list, different types of headings being recognized to quickly and accurately associate text (e.g., text identifying one or more problems) with a heading. Unstructured text, which can be difficult to analyze, is reliably consolidated by the use of spell checking (e.g., contextual spell checking), heading identification algorithms, etc. The removal of irrelevant pages reduce computational load and facilitate analysis of the unstructured text. A list of problems, by itself or together with the associated heading, can be output in a manner that allows for automated identification of problems and generation of one or more Hierarchical Condition Categories ("HCCs") for the identified problems.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Various non-limiting embodiments of the present disclosure will now be described to provide an overall understanding of the principles of the structure, function, and use of systems and methods disclosed herein for identifying a problem list section.

Reference to any particular activity is provided in this disclosure only for convenience and not intended to limit the disclosure. A person of ordinary skill in the art would recognize that the concepts underlying the disclosed devices and methods may be utilized in any suitable activity. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Terms like "provider," "merchant," "vendor," or the like generally encompass an entity or person involved in providing, selling, and/or renting items to persons such as a seller, dealer, renter, merchant, vendor, or the like, as well as an agent or intermediary of such an entity or person. An "item" generally encompasses a good, service, or the like having ownership or other rights that may be transferred. As used herein, terms like "user" or "customer" generally encompasses any person or entity that may desire information, resolution of an issue, purchase of a product, or engage in any other type of interaction with a provider. The term "browser extension" may be used interchangeably with other terms like "program," "electronic application," or the like, and generally encompasses software that is configured to interact with, modify, override, supplement, or operate in conjunction with other software.

As used herein, a "machine-learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

Training the machine-learning model may include one or more machine-learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc. After training the machine-learning mode, the machine-learning model may be deployed in a computer application for use on new input data that the machine-learning model has not been trained on previously.

FIG. 1 is a diagram showing an example of a system that is capable of section identification from unstructured text (e.g., a system for identifying a problem list section), according to some embodiments of the disclosure. As shown in FIG. 1, an environment 100 facilitates processing and analysis of documents, and in particular, medical record documents or MRs 165. Environment 100 includes a heading analysis system 110, one or more medical record systems 160, one or more coding systems 170, and a network 180 that facilitates communication between heading analysis system 110, medical record systems 160, and/or coding systems 170.

In embodiments, various elements of environment 100 communicate with each other through the network 180. Communication infrastructure of environment 100 supports a variety of different communication protocols and communication techniques. Network 180 of environment 100 includes one or more networks such as a data network, a wireless network, a telephony network, or any combination thereof. It is contemplated that the data network is any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network is, for example, a cellular communication network and employs various technologies including 5G (5th Generation), 4G, 3G, 2G, Long Term Evolution (LTE), wireless fidelity (Wi-Fi), Bluetooth®, Internet Protocol (IP) data casting, satellite, mobile ad-hoc network (MANET), and the like, or any combination thereof.

Heading analysis system 110 includes one or more components that analyze medical records 165 received from medical record systems 160 via network 180. Heading analysis system 110 includes, for example, a character recognition module 120, a sentence identifying module 130, a heading identifying module 140, and a relevant section extracting module 150. The character recognition module 120 receives MRs 165 as inputs, and processes the received MRs 165 to generate unstructured text as an output.

Sentence identifying module 130 analyzes the unstructured text from character recognition module 120. For example, sentence identifying module 130 reviews the unstructured text to determine whether the text includes one or more sentences. Sentence identifying module 130 can output any identified sentences and/or modify the unstructured text based on the identified sentences. As used herein "outputting" is understood to include creating one or more documents stored in a memory of a system, modifying one or more documents, storing information in a non-volatile memory, transmitting information over network 180, temporarily storing data in RAM, etc.

Heading identifying module 140 is configured to analyze unstructured text for language associated with a heading. In one embodiment, heading identifying module 140 analyzes unstructured text that includes sentences that were identified by sentence identifying module 130. In other embodiments, heading identifying module 140 analyzes unstructured text directly output from character recognition module 120.

Heading identifying module 140 can identify headings that are associated with problems. These headings can be output by heading identifying module 140, with the remaining unstructured text, to relevant section extracting module 150. These headings are identified based on comparison with a list of known headings, in some embodiments. The list of known headings can be generated by heading analysis system 110 itself. In other embodiments, the list of known headings can be generated in advance and provided to heading analysis system 110. The list of known headings can be modified (e.g., added to) by heading analysis system 110. In some embodiments, heading identifying module 140 is embodied as one or more machine learning models that can modify the list of known headings.

Relevant section extracting module 150 can analyze the identified headings and determine which, if any, of the unstructured text should be associated with a respective heading. This is performed, for example, by comparing each identified heading to a dataset containing words and/or phrases that are known to be associated with headings for problem lists (e.g., by a similarity analysis), as described below. When a problem list heading is identified, unstructured text following this heading and preceding a later heading that is not a problem list heading (e.g., as the later heading does not match with the contents of the data after performing a similarity analysis or other processing technique), can be associated with the problem list heading.

Once groups of unstructured text are associated with respective headings, this information can be used by system 110 to output lists of potential problems, remove irrelevant data from the unstructured text, and perform other tasks. Unstructured text suitable for removal as being irrelevant includes text following a non-problem list heading and/or additional text that is not associated with a problem list heading. The output from relevant section extracting module 150, including relevant data (e.g., relevant unstructured text and, if desired, one or more problem list headings associated with the relevant text) can be transmitted by network 180 to coding systems 170. Coding systems 170 include, in some examples, devices that have programming that facilitate medical coding. Specifically, coding systems 170 enable the identification of Hierarchical Condition Categories ("HCCs") for problems, the problems being present in the data received from heading analysis system 110 via network 180.

Relevant section extracting module 150 is able to analyze unstructured text that is associated with a particular heading, the text being output from heading identifying module 140. Relevant section extracting module 150 is configured to perform analyses that enable identification of relevant sections, the relevant sections being text associated with a heading for a problem list. Relevant section extracting module 150 removes irrelevant data, including irrelevant sections, when desired, reducing the amount of data that is output for downstream processing.

Medical record systems 160 include computing systems that are enabled to generate, modify, and output one or more MRs 165 or other type of electronic document. These computing systems are associated with one or more types of entities, including medical care providers (e.g., hospitals, doctor's offices, urgent care centers, accountable care organizations, etc.), insurance companies, technology providers, governmental agencies, and others. Exemplary MRs 165 created and/or modified by medical record systems 160 of these entities include information, such as one or more of: a patient identifier (e.g., medical record number (MRN)), admission and/or readmission data, discharge data, diagnosis data, treatment data, patient demographic data (e.g., date of birth, age, residence data, etc.), hospital demographic data, insurance data, authorization data (e.g., insurance prior authorization, etc.), critical care document (CCD) summary data, admission, discharge, transfer (ADT) data, health level seven (HL7) messaging data, insurance claims data, disease indicators (Systematized Nomenclature of Medicine-Clinical Terms (SNOMED), etc.), at least one admission date, readmission date(s), etc.

At least some of the MRs 165 generated with medical record systems 160 contain one or more problems associated with an individual. MRs 165 can take various forms, such as text-based content, tables, spreadsheets, slides, and/or images. MRs can also exist in various formats, such as an unstructured data format (e.g., plain text), or a data format that, in at least some electronic documents, is structured (e.g., RTF, DOC, DOCX, PDF, HTML, XML, PPT, XLS). MRs 165 are managed and stored on one or more devices within the network environment 100, such as local or remote file servers, cloud-based storage services, or other forms of data repositories.

Coding systems 170, like medical record systems 160, are associated with entities that include medical care providers, insurance companies, technology providers, governmental agencies, and others. Coding systems 170, while shown as separate systems that communicate with heading analysis system 110 via network 180, can be included as part of heading analysis system 110. Coding systems 170 include one or more computing systems that are configured to analyze data to identify problems and determine codes that correspond to these problems. In particular, the codes identified with coding systems 170 include International Classification of Diseases and Related Health Problems (ICD-10, ICD-11, etc.) codes, among others. Code identification performed with coding systems 170 are, preferably, fully automated or partially automated. However, code identification can be performed manually, if desired.

Code identification performed with coding systems 170 can include receiving data containing one more potential problems (e.g., from relevant section extracting module 150 of heading analysis system 110, as described below), and identifying codes with the use of a machine-learning model, a neural network, and/or other adaptive processing technique. The machine-learning model, when present, is a trained model, the data for training the model being generated, at least in part, with problem lists identified in the manner described herein.

Figure 2:
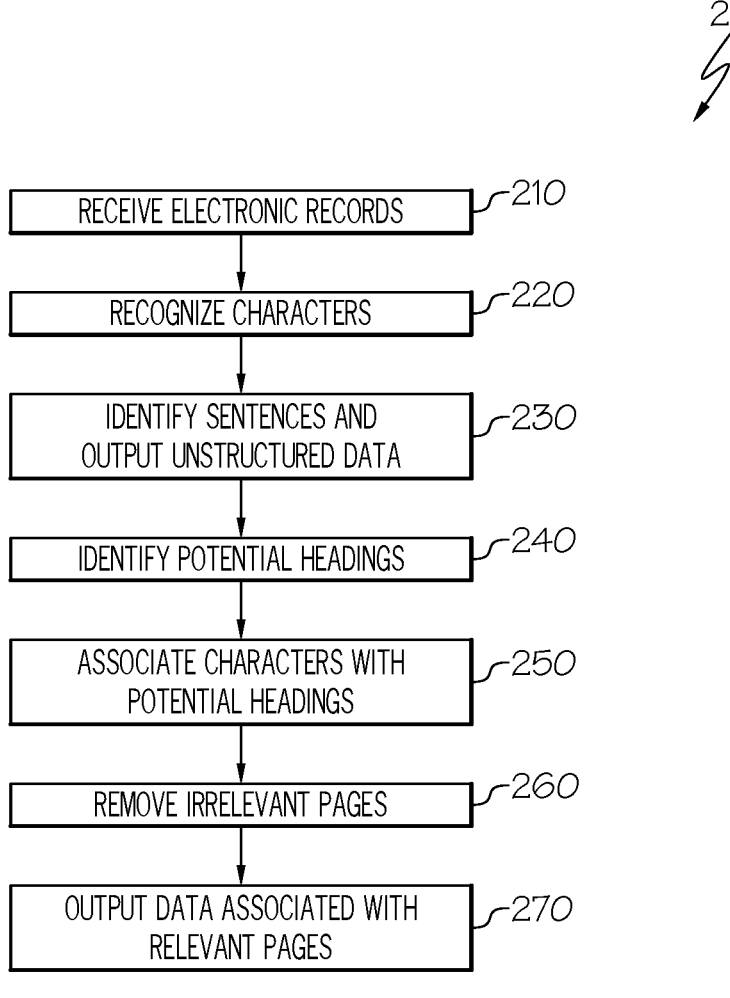
FIG. 2 is a flowchart of an example of a process for identifying a problem list section, according to some embodiments of the disclosure.

FIG. 2 is a flowchart of an example process 200 for identifying one or more problem list sections, according to some embodiments of the disclosure. Details of environment 100, and in particular, heading analysis system 110, will be described in conjunction with process 200.

A step 210 of process 200 includes receiving MRs. The received MRs correspond to MRs 165 generated and/or transmitted by medical record systems 160. These MRs 165 are received by character recognition module 120 of system 110, for example. MRs received in step 210 can be generated by and/or received from a single source or multiple sources. MRs received in step 210 can be either structured or unstructured documents having different styles and layouts, different terminology, and dissimilar content, as well as originating from different sources (e.g., the MRs are received from different medical providers or other entities).

A step 220 includes recognizing characters within the MRs. These characters can be recognized without determining the layout of the MR 165. In some embodiments, character recognition module 120 recognizes characters in one or more MRs 165 by performing a process that includes optical character recognition. Step 220 includes recognizing characters in a structured document (e.g., a document which includes markup data or other data pertaining to rules that represent the type of content or organization of the document, such as the identification of one or more fields or sections, or the category of information contained in a particular portion of the document) or recognizing characters in an unstructured document. In some aspects, the organization of the document is not readily machine-readable. For example, the document may be an image-based document, such as a PDF document, a picture of a physical document, etc. In these and other examples, step 220 involves generating unstructured data (e.g., a text document containing unstructured text), by analyzing an MR 165 which contains at least some layout, markup, metadata, or other information.

As one example, optical character recognition is performed in step 220. Optical character recognition ("OCR") is performed with a suitable lightweight algorithm, an algorithm that processes documents relatively quickly and/or with low processing requirements. Suitable optical character processes can include engines and/or algorithms such as Tesseract OCR, ABBYY FineReader, GOCR, and others.

The engine or algorithm of character recognition module 120 that performs step 220 includes functionality for identifying each character in a document, without the need to process the document to identify structure, such as line spacing, columns, indentations, font, tables, character size, and others. Rather, the engine or algorithm identifies individual characters themselves. The characters identified by the engine or algorithm preferably includes at least English-language characters, other Latin characters, numerals, Asian-language characters, and others. In particular, the engine or algorithm is capable of identifying characters associated with an ISO 15924 code.

While the engine or algorithm, in at least some embodiments, does not identify existing structure in each MR 165, the engine or algorithm can be capable of identifying sentence separators. Sentence separators identified by the engine or algorithm of character recognition module 120 include full stops (e.g., periods), next line indicators (e.g., line breaks, which can be represented by two or more spaces), punctuation marks (e.g., colons, semicolons), and others. Step 210 can include outputting the characters identified with the OCR engine or algorithm to sentence identifying module 130. This can include writing the characters into a memory associated with system 110 and/or generating or modifying one or more documents containing the unstructured characters identified with module 120.

A step 230 includes further processing the documents or other data representing the characters that were identified in step 220. This further processing may include identifying one or more sentences present in the data. As one example, full stops can be identified based on periods present in the data output by the OCR engine or algorithm. During step 230, double spaces and/or punctuation marks can also be identified. The presence of a full stop or two or more spaces can be correlated with a new line character, for example. These new line characters can be used as indicators for dividing the text corpus into sentences.

In some embodiments, step 230 includes separating the document or data, which contains the recognized characters, including a series of sentences and/or a series of phrases. Each sentence of the separated document is defined by a full stop and/or by two or more spaces contained in data output by the Tesseract OCR algorithm.

Identified sentences or phrases can be evaluated with a spell-checking algorithm that identifies words that belong to the English language or other languages (e.g., by comparing words present in the sentences and/or phrases with words contained in database(s) for English and other languages, including medical terminology). Preferably, the spell-checking algorithm is configured for performing a contextual spell check that evaluates words based on nearby words and words in the same sentence. Suitable contextual spell-checking algorithms can also perform analyses based on the purpose of the document (e.g., the status of the document as a MR), etc. An example spell-checking algorithm is Spark NLP, but other algorithms are also suitable. Additionally, while there are advantages in executing one or more spell-checking operations, these operations are optional and can be omitted, if desired, to reduce processor overhead and/or reduce processing time.

Step 240 includes identifying potential headings included in the data from steps 220 and/or 230. Headings are be identified in a process that, advantageously, requires relatively minimal processing time and resources. As one example, one or more words or phrases of a possible problem list heading are compared to a dataset (e.g., a list) containing words or phrases that are known to be associated with problem list headings (referred to herein as a "problem heading list" or "list of known headings"). Step 240 may include performing a similarity analysis in which exact matches and close matches between the dataset and the one or more words or phrases of the unstructured text are identified. This similarity analysis may, in some embodiments, be limited to exact matches of one more words. In other embodiments, the similarity analysis may identify similar words or phrases (e.g., by use of a regex algorithm, natural language algorithm, etc.). In other embodiments, a machine learning model may be configured to perform the similarity analysis. A suitable machine learning algorithm may have been trained based on prior similarity analyses.

Suitable problem heading lists can be generated as part of process 200 or prior to performing process 200. In particular, one or more problem heading lists are created prior to performing process 200 using, for example, one or more of the above-described similarity analyses. An example process 400 for generating a problem heading list is described below with respect to FIGS. 4 and 5. As understood, one or more steps of process 400 can be performed as part of process 200.

In one example, a problem heading list includes single words, such as "problem," "problems," "diagnosis," etc., these words being headings in the dataset containing a problem heading list. In another example, a dataset containing a problem heading list includes both single words and phrases (two or more words), such as the phrases "problem list," "progress notes," "past medical history," "patient active," and others which are headings in the problem heading list. Suitable algorithms can scan the unstructured text for the presence of potential headings by reviewing both single words and phrases.

In addition to identifying potential problem list headings, step 240 includes identifying other potential headings, including non-problem headings (headings that are not associated with a list of problems) with heading identifying module 140. These headings are identified by comparing words or phrases of a possible non-problem heading with a list of words or phrases that are known to be associated with headings other than problem list headings (referred to herein as a "non-problem heading list"). Additionally or alternatively, a possible non-problem heading can be identified without the use of a non-problem heading list (e.g., by identifying non-problem headings based on one or more sentences present in the unstructured text, the non-problem heading containing words and/or phrases that are absent from a problem heading list).

The entire text corpus of the MR, which includes all of the unstructured text extracted as described above, is evaluated by heading identifying module 140 for the presence of single words and phrases that match words and phrases in the problem heading list and words and phrases in the non-problem heading list, resulting in identification of all potential headings in the text corpus of the MR.

In step 240, all of the unstructured text in the MR is categorized by heading identifying module 140 as being a potential problem list heading, a potential non-problem heading, or text that is not a heading (referred to herein as "non-heading text"). The category of the text is known, for example, based on whether the text was associated with the problem heading list, the non-problem heading list, or neither of these lists.

In a step 250, all non-heading text is evaluated to determine if the non-heading text is associated with a problem list heading. First, the non-heading text is associated into sections with at least some, and in some embodiments all, of the sections spanning a pair of headings. In example MRs 165, one or more sections will follow a problem list heading, while one or more other sections will follow a non-problem heading.

Step 250 is performed by analyzing each section to determine whether the section is relevant or irrelevant. Prior to performing step 250, each problem list heading is associated with non-heading text, forming one or more sections that include a problem list heading and text that is likely to identify one or more problems. These headings and text together form a relevant section that can be extracted with relevant section extracting module 150. Relevant section extracting module 150 identifies the end of the section by the presence of a non-problem heading, for example.

Preferably, all relevant sections are identified by relevant section extracting module 150 during step 250. The remaining text is determined to be irrelevant, either because this text is not associated with a problem list heading, or because this text was determined by relevant section extracting module 150 to be associated with a non-problem heading. Thus, irrelevant text can be affirmatively identified or eliminated.

A step 260 advantageously includes removing the irrelevant sections or extracting the relevant sections, these processes being considered equivalent to each other. For some MRs, the irrelevant sections can form most of the pages of the MR. Thus, for at least some MRs, the relevant sections are less than 50% of the original MR, less than 25% of the MR, or even less than 10% of the MR.

In some aspects, relevant section extracting module 150 can identify at least one irrelevant section without the need to identify an associated non-problem heading. This can be performed by limiting the number of consecutive pages in an MR that are permitted to be associated with a problem list heading. In some aspects, a maximum predetermined number of pages can be set. For example, if a value of "3" is set as the maximum number of pages, only three pages of text, or less, is permitted to be associated with the problem list heading as a relevant section, and one or more subsequent pages are identified as being irrelevant.

In some examples, the maximum number of the pages can be the same for each word or phrase in the problem heading list. Thus, continuing the example of a maximum value of "3," only text present within the three pages following headings such as "active problems," "current problems," "problem," and "problem list" is permitted to be identified as relevant.

In other examples, the maximum number of pages can change for at least some of the words and phrases in the problem heading list. In a specific example, the maximum number of pages for "active problems," "current problems," "problem," and "problem list" may be two, one, five, and five (or in some embodiments, ten), respectively. These values are set based on, for example, a statistical distribution determined by analyzing a plurality of different MRs from different sources (e.g., different medical providers).

The use of a predetermined maximum number of pages is advantageous in that it allows relevant section extracting module 150 to avoid false positives. For example, when the unstructured text under analysis has a distorted or otherwise unidentified non-problem heading, extracting module 150 is still able to remove at least some of the irrelevant text.

In some embodiments, relevant section extracting module 150 can identify at least one irrelevant section without an associated non-problem heading. This can be performed by limiting the number of consecutive pages in a MR that are permitted to be associated with a problem list heading. In some aspects, a maximum predetermined number of pages can be set. For example, if a value of "3" is set as the maximum number of pages, only three pages of text, or less, is permitted to be associated with the problem list heading as a relevant section of text, and one or more subsequent pages are identified as being irrelevant.

In some embodiments, step 260 includes analyzing text associated with a problem list heading to confirm relevance. Text (e.g., a text section) following a problem list heading is analyzed, for example, using a chunk count approach and/or an inter-chunk distance approach.

In these approaches, the unstructured (e.g., OCR-generated) text that was determined as being relevant according to the above description of method 200, is passed through an ICD (International Classification of Diseases and Related Health Problems) code identifier pipeline. This pipeline may be created with a natural language processing engine, such as Spark NLP, and is configured in some embodiments to separate sentences into chunks. The ICD code identifier pipeline can determine the presence of one or more medical diagnosis codes in the chunks of text, or text section, following a potential problem heading, and count the chunks that correspond to a medical diagnosis code. The ICD code identifier pipeline can also calculate the average distance between chunks that match with a medical diagnosis code. As understood, the presence of a large number of medical codes following a heading indicates that the heading was correctly identified as a heading of a problem list.

A relatively low chunk count can indicate that a text section is not relevant and can potentially be removed. In one example, a threshold number of chunks is seven chunks per page. Thus, pages having fewer than this threshold number of chunks can be removed as irrelevant to eliminate false positives. Inter-chunk distance, the average distance between chunks containing medical codes, can further eliminate false positive pages. As above, the inter-chunk distance can be compared to a threshold. Pages or sections that do not meet this predetermined threshold can be removed as being irrelevant.

The relevant text can be output for further processing in a step 270. This further processing can be performed manually, automatically, or as a combination of manual and automated processes. In one example, step 270 includes outputting the relevant text to one or more coding systems 170 (FIG. 1). Subsequently, the coding systems 170 can automatically and/or manually code problems identified in the relevant sections. As indicated above, for at least some MRs 165, many pages are removed. In some MRs 165, most of the pages or sections are removed as being irrelevant, facilitating the processing performed in step 270. In automated processes for coding and identifying problems, processing requirements can be significantly reduced by the removal of irrelevant pages during step 260. This can improve the speed at which step 270 can be performed, and can enable more processing-intensive analyses (e.g., the use of a trained machine learning model).

FIG. 3 is a specific example showing a method 300 illustrating the processes performed during method 200 and corresponding methods. As shown in FIG. 3, an initial step includes receiving an unprocessed MR 310 or other electronic document containing structured text. As understood, the depiction in FIG. 3 is a portion or snapshot of a single page of the MR, which in some examples can include 20 pages of text or more.

In the example shown in FIG. 3, unprocessed MR 310 contains headings that are not problem list headings: "Communicable Diseases" and "Immunizations". The MR also contains one example problem list heading, "Current Problems." The unprocessed MR 310 also includes non-heading text. The non-heading text includes "Last reviewed on," "Reportable health conditions, NEGATIVE," "Dependence on other enabling machines," "Metabolic syndrome," and "PNEUMOVAX 23," as some examples.

The unprocessed MR 310 is evaluated via processing 320 such that characters are recognized, sentences are separated, and potential headings are identified. Following processing, MR 330 includes the non-problem headings, problem list heading, and non-heading text, all in an unstructured format, and potentially with one or more errors or distortions introduced by the processing 320.

Further processing of MR 330 results in the identification of the non-problem headings and problem list headings, as well as association of the non-heading text to each of these headings, as described above. In the illustrated example, non-heading text associated with a non-problem heading includes "Last reviewed on," "PNEUMOVAX 23," etc.

Irrelevant text is removed by processing 340, which for some MRs 165 involves removal of entire pages, resulting in one or more extracted relevant pages 350. Processing 340 can be performed as described above with respect to step 260. This data, containing relevant pages 350, can be output to another system as described above, or processed directly by system 110 to identify problems.

Figure 4:
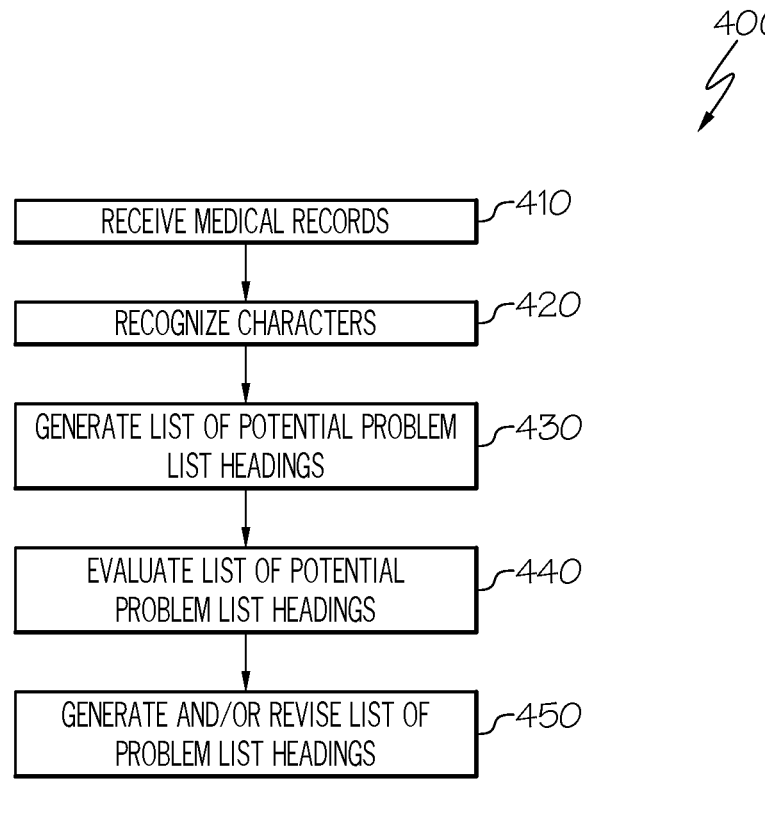
FIG. 4 is a flowchart of an example process for generating and/or revising a list of headings, according to some embodiments of the disclosure.

FIG. 4 is a flowchart illustrating a method 400. If desired, method 400 is performed as part of method 300. However, as described below, method 400 can be performed prior to performing method 300, and can be used to generate and/or update a list of problem list headings, also referred to herein as "a list of candidate headings." Method 300 and method 400 can be performed iteratively, and can therefore improve the accuracy of method 300 over time.

A step 410 of method 400 includes receiving MRs. Step 410 can be performed in the same manner as described above with respect to step 210. Advantageously, the MRs received during step 410 are from different sources, have different formats, etc., to provide a suitable sample size for processing and generation of a problem heading list.

A step 420 of method 400 includes recognizing characters in MRs that were received in step 410. Step 420 is performed in the manner described above with respect to step 220, and is performed for each MR received in step 210.

A step 430 includes generating the list of problem list headings, or list of candidate headings. This list includes words and/or phrases that are candidates for inclusion in a problem heading list, as employed by method 200, for example. The process of generating the list of candidate headings includes, in some examples, identifying sentences in the characters recognized during step 420. Sentences can be recognized in a manner similar to that of step 230, as described above.

These candidate problem list headings can be identified by identifying words and/or phrases that meet one or more criteria. In particular, candidate problem list headings are identified by analyzing each sentence for words or phrases that satisfy one or more criteria associated with a problem (referred to herein as "problem-word criteria").

As one example, problem-word criteria include a word or phrase that is frequently present in the heading for a problem list section of a MR. This criteria can be developed, for example, by manually or automatically identifying words or phrases that are possibly associated with a problem list heading, and subsequently analyzing how often these words or phrases occur in the presence of words or phrases that are known to refer to problems.

As another example, the problem-word criteria include the identification of a word or phrase that is present across multiple documents. Particular words and phrases such as "problem," "problem list," and others, are present in a certain percent of MRs that contain a problem list. Based on this, it is possible to establish a predetermined frequency value (e.g., 15%), and determine whether a word or phrase that is under consideration for inclusion in a problem heading list at least as frequently as specified.

As yet another example, the problem-word criteria include presence of a word or phrase on a predetermined number of pages in a particular MR 165. The predetermined number of pages can be one (e.g., presence of a word or phrase on no more than one page), two (e.g., the presence of a word or phrase on no more than two pages), etc.

As yet another example, the problem-word criteria include presence of the word or phrase in a sentence having a length (e.g., a number of words) that is less than a threshold value. For example, a suitable word count criterion is a word count of less than seven words.

Step 430 can include receiving a prompt word or "seed" word, in some embodiments. The seed word can be received from an automated system or by manual input from a user, and is used to identify similar words in the characters and sentences processed in steps 420 and 430. As an example, the seed word is used as an input to a regular expression engine ("regex"). Similar words and phrases are identified with regex, these similar words or phrases forming candidates for inclusion in a problem heading list. The seed word can therefore assist in identifying candidate words or phrases in the list of candidate headings.

In some embodiments, step 430 includes further expanding the list of candidate headings. This can be performed by a fuzzy matching approach or other algorithm that identifies text that is similar to an input (e.g., the heading "Problem List"). One suitable fuzzy matching approach is a Soundex algorithm, which identifies words and phrases that have phonetic similarities. For example, the known problem list heading "Problem List" may be automatically generated or manually input. One or more MRs 165 may include headings such as: "History of Present Illness" and "Immunization." These phrases can be analyzed to determine their similarity to the known problem list heading to determine if one or more should be included in the list of candidate headings.

Continuing with the above example, a cosine similarity analysis is performed for "History of Present Illness" and "Immunization," to quantitatively determine how similar these terms are to the know problem list heading. In this example, "History of Present Illness" has a cosine similarity scores of 0.24, while "Immunization" has a cosine similarity score of −0.038. These values are compared to a predetermined threshold value, with phrases exceeding this threshold score being added to the list of candidate headings. Given an example threshold value of 0.15, the phrase "History of Present Illness" would be added to the list of candidate headings, while the heading "Immunization" would not be included in the list of candidate headings.

Additional or alternative processes can be employed to generate the list of candidate headings. One example is shown in FIG. 5, which is a flowchart of a method 500 that, in at least some embodiments, is performed as a portion or an entirety of step 440 of method 400.

Method 500 can advantageously identify words or phrases for inclusion in a list of candidate headings based on the presence of tables of contents and/or indices in MRs. Method 500 can include generating unstructured text from the structured text of one or more unprocessed MRs 510. This unstructured text of a processed MR 520 is then analyzed for the presence of a table of contents and/or an index.

A table of contents or index can be identified by an automated process or a manual process. In the example of a manual process, a sequence of characters or regex, is input by a user to assist in the identification of the table of contents or index. For example, a user may manually input "index," "table of contents," "contents," etc. As understood, these inputs may be stored in a memory or otherwise automatically entered.

In an example, system 100 automatically searches the processed MR 520 for the phrase "table of contents," which is identified as shown in FIG. 5. Based on the identification of a table of contents, method 500 includes determining that at least some language following the phrase "table of contents" is a potential heading. These terms or phrases can be extracted to form a list 530 of terms and/or phrases that are used to generate or update the list of candidate headings in step 430 (FIG. 4).

A step 440 of method 400 includes evaluating the list of potential problem list headings generated in step 430. When step 440 is performed, this evaluation includes eliminating words or phrases from the list that are not likely to be associated with one or more problems. Step 440 can include using one or more of the above-described techniques, such as use of an ICD code identifier pipeline, cosine distance scoring, or if desired, manual removal of one or more candidate headings, to avoid the inclusion of undesired words or phrases from the problem heading list that will be generated or updated based on the list of potential problem list headings.

A step 450 of method 400 includes generating the above-described list of problem list headings. Additionally or alternatively, step 450 includes updating or otherwise revising an existing list of problem list headings. The result of step 450 can be a finalized list of words and/or phrases used to identify problem list headings, or an updated list, that was created based at least in part on the list of candidate headings. This finalized list is suitable for use by heading analysis system 110, and in particular, heading identifying module 140, as described above, during method 200.

In general, any process or operation discussed in this disclosure is understood to be computer-implementable, such as the process illustrated in FIGS. 2-5 are performed by one or more processors of a computer system as described herein. A process or process step performed by one or more processors is also referred to as an operation. The one or more processors are configured to perform such processes by having access to instructions (e.g., software or computer-readable code) that, when executed by one or more processors, cause one or more processors to perform the processes. The instructions are stored in a memory of the computer system. A processor is a central processing unit (CPU), a graphics processing unit (GPU), or any suitable type of processing unit.

A computer system, such as a system or device implementing a process or operation in the examples above, includes one or more computing devices. One or more processors of a computer system are included in a single computing device or distributed among a plurality of computing devices. One or more processors of a computer system are connected to a data storage device. A memory of the computer system includes the respective memory of each computing device of the plurality of computing devices.

Figure 6:
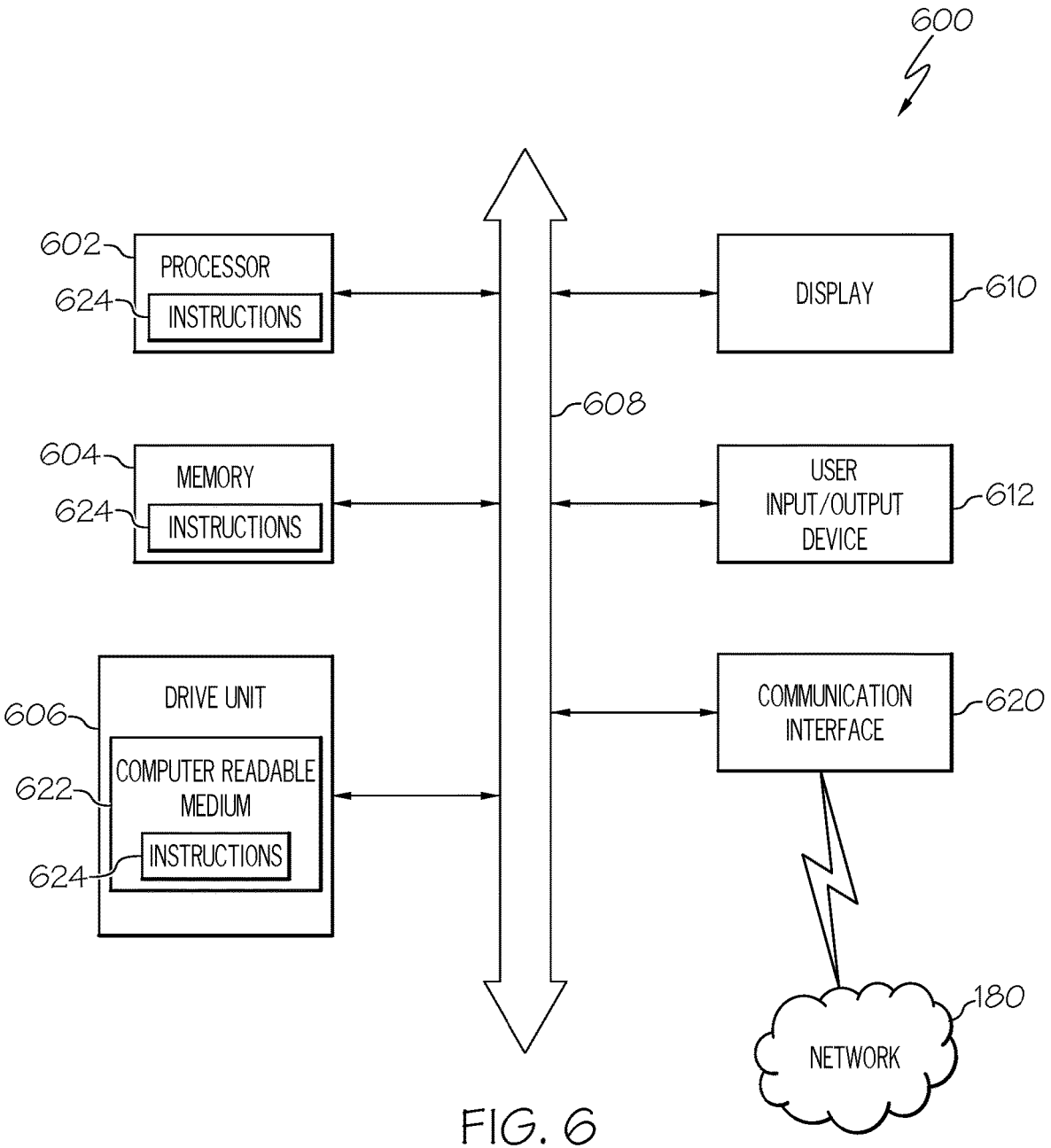
FIG. 6 illustrates an implementation of a computer system that executes techniques presented herein, according to some embodiments of the disclosure.

FIG. 6 illustrates an implementation of a computer system that executes techniques presented herein. The computer system 600 includes a set of instructions that are executed to cause the computer system 600 to perform any one or more of the methods or computer based functions disclosed herein. The computer system 600 operates as a standalone device or is connected, e.g., using a network, to other computer systems or peripheral devices.

Unless specifically stated otherwise, as apparent from the following discussions, it is appreciated that throughout the specification, discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" refers to any device or portion of a device that processes electronic data, e.g., from registers and/or memory to transform that electronic data into other electronic data that, e.g., is stored in registers and/or memory. A "computer," a "computing machine," a "computing platform," a "computing device," or a "server" includes one or more processors.

In a networked deployment, the computer system 600 operates in the capacity of a server or as a client user computer in a server-client user network environment, or as a peer computer system in a peer-to-peer (or distributed) network environment. The computer system 600 is also implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the computer system 600 is implemented using electronic devices that provide voice, video, or data communication. Further, while the computer system 600 is illustrated as a single system, the term "system" shall also be taken to include any collection of systems or sub-systems that individually or jointly execute a set, or multiple sets, of instructions to perform one or more computer functions.

As illustrated in FIG. 6, the computer system 600 includes a processor 602, e.g., a central processing unit (CPU), a graphics processing unit (GPU), or both. The processor 602 is a component in a variety of systems. For example, the processor 602 is part of a standard personal computer or a workstation. The processor 602 is one or more processors, digital signal processors, application specific integrated circuits, field programmable gate arrays, servers, networks, digital circuits, analog circuits, combinations thereof, or other now known or later developed devices for analyzing and processing data. The processor 602 implements a software program, such as code generated manually (i.e., programmed).

The computer system 600 includes a memory 604 that communicates via bus 608. The memory 604 is a main memory, a static memory, or a dynamic memory. The memory 604 includes, but is not limited to computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 604 includes a cache or random-access memory for the processor 602. In alternative implementations, the memory 604 is separate from the processor 602, such as a cache memory of a processor, the system memory, or other memory. The memory 604 is an external storage device or database for storing data. Examples include a hard drive, compact disc ("CD"), digital video disc ("DVD"), memory card, memory stick, floppy disc, universal serial bus ("USB") memory device, or any other device operative to store data. The memory 604 is operable to store instructions executable by the processor 602. The functions, acts, or tasks illustrated in the figures or described herein are performed by the processor 602 executing the instructions stored in the memory 604. The functions, acts, or tasks are independent of the particular type of instruction set, storage media, processor, or processing strategy and are performed by software, hardware, integrated circuits, firmware, micro-code, and the like, operating alone or in combination. Likewise, processing strategies include multiprocessing, multitasking, parallel processing, and the like.

As shown, the computer system 600 further includes a display 610, such as a liquid crystal display (LCD), an organic light emitting diode (OLED), a flat panel display, a solid-state display, a cathode ray tube (CRT), a projector, a printer or other now known or later developed display device for outputting determined information. The display 610 acts as an interface for the user to see the functioning of the processor 602, or specifically as an interface with the software stored in the memory 604 or in the drive unit 606.

Additionally or alternatively, the computer system 600 includes an input/output device 612 configured to allow a user to interact with any of the components of the computer system 600. The input/output device 612 is a number pad, a keyboard, a cursor control device, such as a mouse, a joystick, touch screen display, remote control, or any other device operative to interact with the computer system 900.

The computer system 600 also includes the drive unit 606 implemented as a disk or optical drive. The drive unit 606 includes a computer-readable medium 622 in which one or more sets of instructions 624, e.g. software, is embedded. Further, the sets of instructions 624 embodies one or more of the methods or logic as described herein. The sets of instructions 624 resides completely or partially within the memory 604 and/or within the processor 602 during execution by the computer system 900. The memory 604 and the processor 602 also include computer-readable media, as discussed above.

In some systems, computer-readable medium 622 includes the set of instructions 624 or receives and executes the set of instructions 624 responsive to a propagated signal so that a device connected to network 630 communicates voice, video, audio, images, or any other data over the network 630. Further, the sets of instructions 624 are transmitted or received over the network 630 via the communication port or interface 620, and/or using the bus 608. The communication port or interface 620 is a part of the processor 602 or is a separate component. The communication port or interface 620 is created in software or is a physical connection in hardware. The communication port or interface 620 is configured to connect with the network 630, external media, the display 610, or any other components in the computer system 600, or combinations thereof. The connection with the network 630 is a physical connection, such as a wired Ethernet connection, or is established wirelessly as discussed below. Likewise, the additional connections with other components of the computer system 600 are physical connections or are established wirelessly. The network 630 alternatively be directly connected to the bus 608.

While the computer-readable medium 622 is shown to be a single medium, the term "computer-readable medium" includes a single medium or multiple media, such as a centralized or distributed database, and/or associated caches and servers that store one or more sets of instructions. The term "computer-readable medium" also includes any medium that is capable of storing, encoding, or carrying a set of instructions for execution by a processor or that causes a computer system to perform any one or more of the methods or operations disclosed herein. The computer-readable medium 622 is non-transitory, and may be tangible.

The computer-readable medium 622 includes a solid-state memory such as a memory card or other package that houses one or more non-volatile read-only memories. The computer-readable medium 622 is a random-access memory or other volatile re-writable memory. Additionally or alternatively, the computer-readable medium 622 includes a magneto-optical or optical medium, such as a disk or tapes or other storage device to capture carrier wave signals such as a signal communicated over a transmission medium. A digital file attachment to an e-mail or other self-contained information archive or set of archives is considered a distribution medium that is a tangible storage medium. Accordingly, the disclosure is considered to include any one or more of a computer-readable medium or a distribution medium and other equivalents and successor media, in which data or instructions are stored.

In an alternative implementation, dedicated hardware implementations, such as application specific integrated circuits, programmable logic arrays, and other hardware devices, is constructed to implement one or more of the methods described herein. Applications that include the apparatus and systems of various implementations broadly include a variety of electronic and computer systems. One or more implementations described herein implement functions using two or more specific interconnected hardware modules or devices with related control and data signals that are communicated between and through the modules, or as portions of an application-specific integrated circuit. Accordingly, the present system encompasses software, firmware, and hardware implementations.

Computer system 600 is connected to the network 180. The network 180 defines one or more networks including wired or wireless networks. The wireless network is a cellular telephone network, an 802.10, 802.16, 802.20, or WiMAX network. Further, such networks include a public network, such as the Internet, a private network, such as an intranet, or combinations thereof, and utilizes a variety of networking protocols now available or later developed including, but not limited to TCP/IP based networking protocols. The network 180 includes wide area networks (WAN), such as the Internet, local area networks (LAN), campus area networks, metropolitan area networks, a direct connection such as through a Universal Serial Bus (USB) port, or any other networks that allows for data communication. The network 180 is configured to couple one computing device to another computing device to enable communication of data between the devices. The network 180 is generally enabled to employ any form of machine-readable media for communicating information from one device to another. The network 930 includes communication methods by which information travels between computing devices. The network 180 is divided into sub-networks. The sub-networks allow access to all of the other components connected thereto or the sub-networks restrict access between the components. The network 180 is regarded as a public or private network connection and includes, for example, a virtual private network or an encryption or other security mechanism employed over the public Internet, or the like.

In accordance with various implementations of the present disclosure, the methods described herein are implemented by software programs executable by a computer system. Further, in an example, non-limited implementation, implementations can include distributed processing, component/object distributed processing, and parallel processing. Alternatively, virtual computer system processing can be constructed to implement one or more of the methods or functionality as described herein.

Although the present specification describes components and functions that are implemented in particular implementations with reference to particular standards and protocols, the disclosure is not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure is implemented using any appropriate techniques for implementing the functionality described herein. The disclosure is not limited to any particular programming language or operating system.

It should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention are practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications are made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

The present disclosure furthermore relates to the following aspects.

Example 1. A computer-implemented method for identifying a problem list section, the method comprising: receiving, by one or more processors, the electronic document; generating, by the one or more processors and based on applying an optical character recognition algorithm to the electronic document, unstructured text; identifying, by the one or more processors, one or more problem list words in the unstructured text, the one or more problem list words belonging in a dataset for identifying a presence of a problem list section; associating, by the one or more processors, a portion of the unstructured text that corresponds to the one or more problem list words in the unstructured text with the problem list section; and outputting, by the one or more processors, at least a portion of the problem list section.

Example 2. The computer-implemented method of example 1, further including removing one or more irrelevant portions of the unstructured text that are not associated with the one or more problem list words, the one or more irrelevant portions being identified according to one or more criteria that include: the presence of text following a heading that is not associated with a problem list word, or the presence of text on one or more pages following a predetermined maximum number of pages after the one or more problem list words.

Example 3. The computer-implemented method of example 1 or example 2, wherein the portion of the unstructured text is located between a problem list heading and a non-problem list heading.

Example 4. The computer-implemented method of example 3, wherein the problem list heading includes one or more words having one or more respective cosine similarity scores that represent similarity with one or more words contained in a known problem list heading.

Example 5. The computer-implemented method of any of the preceding examples, wherein the dataset includes words and/or phrases that are associated with problem list headings that precede a problem list, the one or more problem list words in the unstructured text being identified based on a similarity analysis with the dataset.

Example 6. The computer-implemented method of example 5, wherein the dataset was generated based on a table of contents or an index identified in one or more medical records.

Example 7. The computer-implemented method of example 5, wherein the dataset was generated based on one or more other electronic documents.

Example 8. A system for identifying a problem list section, the system comprising: a memory storing instructions; and a processor executing the instructions to perform a process including: receiving an electronic document; generating, based on applying an optical character recognition algorithm to the electronic document, unstructured text; identifying one or more problem list words in the unstructured text, the one or more problem list words belonging in a dataset for identifying a presence of a problem list section; associating a portion of the unstructured text that corresponds to the one or more problem list words in the unstructured text with the problem list section; and outputting at least a portion of the problem list section.

Example 9. The system of example 8, wherein the instructions cause the characters to be recognized without determining a layout of the electronic document.

Example 10. The system of example 8 or 9, wherein the instructions cause removal of one or more irrelevant portions of the unstructured text that are not associated with the one or more problem list words, the one or more irrelevant portions being identified according to one or more criteria that include: the presence of text following a heading that is not associated with a problem list word, or the presence of text on one or more pages following a predetermined maximum number of pages after the one or more problem list words.

Example 11. The system of example 8, 9, or 10, wherein the portion of the unstructured text is located between a problem list heading and a non-problem list heading.

Example 12. The system of example 11, wherein the problem list heading includes one or more words having one or more respective cosine similarity scores that represent similarity with one or more words contained in a known problem list heading.

Example 13. The system of example 8, wherein the dataset includes words and/or phrases that are associated with problem list headings that precede a problem list, the one or more problem list words in the unstructured text being identified based on a similarity analysis with the dataset.

Example 14. The system of example 13, wherein the dataset was generated based on one or more other electronic documents.

Example 15. A computer-implemented method for generating a list of problem list headings, the method comprising: receiving, by one or more processors, an electronic document; recognizing, by the one or more processors, characters present in the electronic document by implementing an optical character recognition algorithm that receives the electronic document as an input and produces unstructured text as an output; identifying, by the one or more processors, characters forming words and/or phrases of one or more headings that each indicate a presence of a problem list in the unstructured text output from the electronic document, each of the one or more headings being a potential problem list heading; and generating, by the one or more processors, a list of words and/or phrases that include the one or more potential problem list headings, the list of words and/or phrases forming a list of problem list headings, wherein one or more additional electronic documents are processed based on the list of problem list headings.

Example 16. The computer-implemented method of example 15, further including identifying, by the one or more processors, an index or a table of contents section, wherein the words and/or phrases of the one or more potential problem list headings are identified based on the index or the table of contents section.

Example 17. The computer-implemented method of example 15 or 16, wherein each of the one or more potential problem list headings is identified based on criteria including a presence of the words and/or phrases of the potential problem list heading in multiple electronic documents.

Example 18. The computer-implemented method of example 15, 16, or 17, wherein each of the one or more potential problem list headings is identified based on criteria including a presence of the words and/or phrases of the potential problem list heading no more than once on each page of the electronic document.

Example 19. The computer-implemented method of example 15, 16, 17, or 18, wherein each of the one or more potential problem list headings is associated with a text section that is identified based on criteria including a length of the text section being no more than a predetermined length.

Example 20. The computer-implemented method of example 15, 16, 17, 18, or 19, wherein each of the one or more potential problem list heading is associated with a text section that is identified based on criteria including a presence of one or more conditions that are associated with codes present in the International Classification of Diseases, the one or more conditions following the potential problem list heading.

What is claimed is:

1. A computer-implemented method for extracting a problem list section from an electronic document, the method comprising:

receiving, by one or more processors, the electronic document;

generating, by the one or more processors and based on applying an optical character recognition algorithm to the electronic document, unstructured text;

identifying, by the one or more processors, one or more problem list words in the unstructured text, the one or more problem list words belonging in a dataset for identifying a presence of a problem list section;

associating, by the one or more processors, a portion of the unstructured text that corresponds to the one or more problem list words in the unstructured text with the problem list section;

removing, by the one or more processors, one or more irrelevant portions of the unstructured text that are not associated with the one or more problem list words, the one or more irrelevant portions being identified according to one or more criteria that include:

the presence of text following a heading that is not associated with a problem list word, or the presence of text on one or more pages following a predetermined maximum number of pages after the one or more problem list words; and outputting, by the one or more processors, at least a portion of the problem list section.

2. The computer-implemented method of claim 1, wherein the portion of the unstructured text is located between a problem list heading and a non-problem list heading.

3. The computer-implemented method of claim 2, wherein the problem list heading includes one or more words having one or more respective cosine similarity scores that represent similarity with one or more words contained in a known problem list heading.

4. The computer-implemented method of claim 1, wherein the dataset includes words and/or phrases that are associated with problem list headings that precede a problem list, the one or more problem list words in the unstructured text being identified based on a similarity analysis with the dataset.

5. The computer-implemented method of claim 4, wherein the dataset was generated based on a table of contents or an index identified in one or more medical records.

6. The computer-implemented method of claim 1, wherein the dataset was generated based on one or more other electronic documents.

7. The computer-implemented method of claim 1, wherein the at least a portion of the problem list section includes non-heading text.

8. The computer-implemented method of claim 1, wherein the at least a portion of the problem list section is output for identification of Hierarchical Condition Categories.

9. A system for identifying a problem list section, the system comprising:

one or more processors; and one or more non-transitory computer-readable media storing processor-executable instructions that, when executed by the one or more processors, cause the one or more processors to perform operations including:

receiving an electronic document;

generating, based on applying an optical character recognition algorithm to the electronic document, unstructured text;

identifying one or more problem list words in the unstructured text, the one or more problem list words belonging in a dataset for identifying a presence of a problem list section;

associating a portion of the unstructured text that corresponds to the one or more problem list words in the unstructured text with the problem list section;

removing one or more irrelevant portions of the unstructured text that are not associated with the one or more problem list words, the one or more irrelevant portions being identified according to one or more criteria that include:

the presence of text following a heading that is not associated with a problem list word, or the presence of text on one or more pages following a predetermined maximum number of pages after the one or more problem list words; and outputting at least a portion of the problem list section.

10. The system of claim 9, wherein the instructions cause the characters to be recognized without determining a layout of the electronic document.

11. The system of claim 9, wherein the portion of the unstructured text is located between a problem list heading and a non-problem list heading.

12. The system of claim 11, wherein the problem list heading includes one or more words having one or more respective cosine similarity scores that represent similarity with one or more words contained in a known problem list heading.

13. The system of claim 9, wherein the dataset includes words and/or phrases that are associated with problem list headings that precede a problem list, the one or more problem list words in the unstructured text being identified based on a similarity analysis with the dataset.

14. The system of claim 13, wherein the dataset was generated based on one or more other electronic documents.

15. A computer-implemented method for generating a list of problem list headings, the method comprising:

receiving, by one or more processors, an electronic document;

recognizing, by the one or more processors, characters present in the electronic document by implementing an optical character recognition algorithm that receives the electronic document as an input and produces unstructured text as an output;

identifying, by the one or more processors, characters forming words and/or phrases of one or more headings that each indicate a presence of a problem list in the unstructured text output from the electronic document, each of the one or more headings being a potential problem list heading; and generating, by the one or more processors, a list of words and/or phrases that include the one or more potential problem list headings, the list of words and/or phrases forming a list of problem list headings, wherein one or more additional electronic documents are processed based on the list of problem list headings, including removing one or more irrelevant portions of unstructured text in the one or more additional electronic documents that are not associated with the list of words and/or phrases, the one or more irrelevant portions being identified according to one or more criteria that include:

the presence of text following a heading that is not associated with the list of words and/or phrases, or the presence of text on one or more pages following a predetermined maximum number of pages after the list of words and/or phrases.

16. The computer-implemented method of claim 15, further including identifying, by the one or more processors, an index or a table of contents section, wherein the words and/or phrases of the one or more potential problem list headings are identified based on the index or the table of contents section.

17. The computer-implemented method of claim 15, wherein each of the one or more potential problem list headings is identified based on criteria including a presence of the words and/or phrases of the potential problem list heading in multiple electronic documents.

18. The computer-implemented method of claim 15, wherein each of the one or more potential problem list headings is identified based on criteria including a presence of the words and/or phrases of the potential problem list heading no more than once on each page of the electronic document.

19. The computer-implemented method of claim 15, wherein each of the one or more potential problem list headings is associated with a text section that is identified based on criteria including a length of the text section being no more than a predetermined length.

20. The computer-implemented method of claim 15, wherein each of the one or more potential problem list heading is associated with a text section that is identified based on criteria including a presence of one or more conditions that are associated with codes present in the International Classification of Diseases, the one or more conditions following the potential problem list heading.

\* \* \* \* \*